United States Patent [19]

Scott

[11] Patent Number: 4,552,889
[45] Date of Patent: Nov. 12, 1985

[54] 3-MERCAPTOMETHYL-2-OXO-1-PYRROLIDINE ACETIC ACIDS AND USE FOR HYPERTENSION

[75] Inventor: William L. Scott, Indianapolis, Ind.

[73] Assignee: Eli Lilly and Company, Indianapolis, Ind.

[21] Appl. No.: 502,861

[22] Filed: Jun. 9, 1983

[51] Int. Cl.$^4$ .................... A61K 31/40; C07D 207/12
[52] U.S. Cl. ................................ 514/424; 548/551
[58] Field of Search ............... 548/551; 424/274; 514/424

[56] References Cited

U.S. PATENT DOCUMENTS

| 4,046,889 | 9/1977 | Ondetti et al. | 424/244 |
| 4,052,511 | 10/1977 | Cushman et al. | 424/244 |
| 4,070,361 | 1/1978 | Petrillo, Jr. | 260/293.85 |
| 4,086,338 | 4/1978 | Cushman et al. | 424/244 |
| 4,105,776 | 8/1978 | Ondetti et al. | 424/274 |
| 4,128,653 | 12/1978 | Cushman et al. | 424/267 |
| 4,261,895 | 4/1981 | Wiskott | 260/326.36 |
| 4,283,407 | 8/1981 | Malen et al. | 424/270 |

FOREIGN PATENT DOCUMENTS

| 833 | 2/1979 | European Pat. Off. . |
| 49500 | 4/1981 | European Pat. Off. . |
| 49842 | 4/1981 | European Pat. Off. . |
| 61187 | 9/1982 | European Pat. Off. . |
| 2000508 | 1/1979 | United Kingdom . |
| 2010675 | 7/1979 | United Kingdom . |

OTHER PUBLICATIONS

*Biochemical and Biophysical Research Communications*, 111 (1), 166, (1983).
*J. Med. Chem.*, 25, 250, (1982).
*J. Med. Chem.*, 24, 104, (1981).
Derwent B/12 22,944, abstracting Japanese Patent J5 4019-969.
Derwent B/15 28164, abstracting German Patent DT 2842-100.

Primary Examiner—Richard L. Raymond
Assistant Examiner—D. B. Springer
Attorney, Agent, or Firm—Charles W. Ashbrook; Arthur R. Whale

[57] ABSTRACT

This invention provides for certain lactam derivatives, their pharmaceutical formulations, and a method of treating hypertension.

18 Claims, No Drawings

3-MERCAPTOMETHYL-2-OXO-1-PYRROLIDINE ACETIC ACIDS AND USE FOR HYPERTENSION

BACKGROUND OF THE INVENTION

The octapeptide angiotensin II is a potent pressor agent. It is formed from the decapeptide angiotensin I by the "converting enzyme" or angiotensinase. Converting enzyme has also been shown to degrade the nonapeptide bradykinin which is a vasodilator. Compounds which inhibit angiotensinase can therefore block both the formation of angiotensin II and prevent the degradation of bradykinin. By either or both of these mechanisms, inhibitors of angiotensinase are useful as antihypertensive agents both in animal models and clinically.

European Patent Application Nos. 49,505 and 49,842, *Biochemical And Biophysical Research Communications*, 111 (1), 166 (1983), *J. Med. Chem.*, 25, 250 (1982), and *J. Med. Chem.*, 24, 104 (1981) all describe 3-(mercaptomethyl)-N-lactamacetic acid derivatives which are said to be useful as antihypertensive agents by virtue of their ability to inhibit angiotensin converting enzyme.

SUMMARY OF THE INVENTION

This invention provides substituted lactam derivatives of the formula I

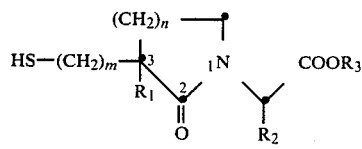

and pharmaceutically acceptable salts thereof wherein
m is 0 or 1;
n is 1, 2, 3, or 4;
$R_1$ is $C_1$–$C_3$ alkyl or benzyl;
$R_2$ is hydrogen or $C_1$–$C_3$ alkyl; and
$R_3$ is hydrogen or $C_1$–$C_3$ alkyl.

The compounds of formula I inhibit angiotensinase. An additional embodiment of this invention therefore includes a method of treating hypertension comprising administering to a mammal suffering from hypertension and in need of treatment an amount of a hypotensively active compound of formula I sufficient to lower blood pressure.

A further aspect of this invention is a pharmaceutical formulation comprising one or more of the biologically active compounds of formula I in combination with a suitable pharmaceutical carrier, diluent, or excipient therefor. The formulations provided by this invention are particularly useful in treating mammals suffering from hypertension.

DETAILED DESCRIPTION AND PREFERRED EMBODIMENT

The term "$C_1$–$C_3$ alkyl" refers to methyl, ethyl, n-propyl, and isopropyl. In formula I when n is 1, 2, 3, and 4, the compounds are 1,3,3-trisubstituted-2-pyrrolidones, -2-piperidones, -ε-caprolactams, and -2-azacyclooctanones, respectively.

A preferred group of compounds of this invention are the compounds of formula I wherein:
(a) m is 1;
(b) n is 1;
(c) $R_1$ is $C_1$–$C_3$ alkyl, especially methyl;
(d) $R_2$ is hydrogen or methyl; and
(e) $R_3$ is hydrogen.

There are two potential asymmetric centers in the compounds of formula I. When $R_2$ is hydrogen, the compounds occur as a simple enantiomeric pair or racemate (dl mixture) by virtue of the single asymmetric center at C-3. When $R_2$ is $C_1$–$C_3$ alkyl, the carbon atom to which $R_2$ is attached also becomes an asymmetric atom and the compounds occur as two racemates. However, one of the two possible stereoisomeric forms of formula I where $R_2$ is $C_1$–$C_3$ alkyl as represented by formula Ia below is preferred.

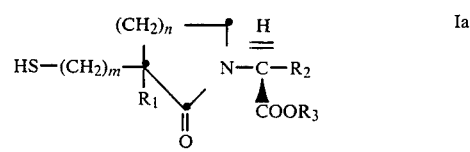

This form is the "S" form and is derived from the l-amino acid via the synthetic procedure described herein. Although the compounds of formula I which are derived from the d- and dl-amino acids are also contemplated in this invention, the compounds with stereoisomeric configuration of formula Ia are preferred and are designated d-l and l-l. Since these two configurations are not mirror images, they can be readily separated, if desired, by methods known in the art, such as high pressure liquid chromatography.

A general procedure for preparing the compounds of formula I is described in Scheme I:

Scheme I

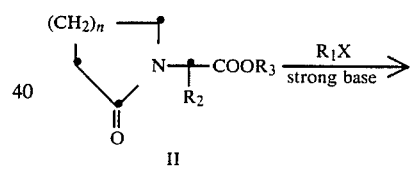

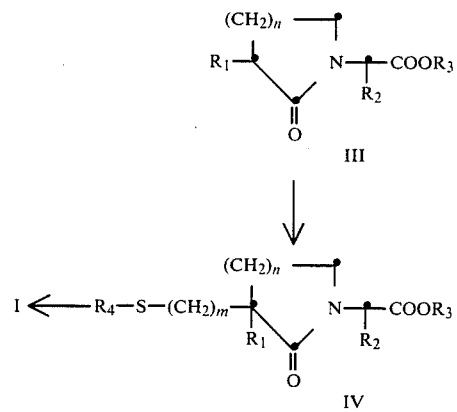

wherein $R_1$, $R_2$, $R_3$, m, and n are the same as described above, $R_4$ is benzyl or 4-methoxybenzyl, and X is chloro, bromo, or iodo.

The preferred sequence involves the alkylation of lactam II with a suitable alkyl or benzylhalide. This procedure generally involves the formation of the anion of II in a nonreactive solvent such as diethyl ether, tetrahydrofuran or 1,2-dimethoxyethane at temperatures from about $-78°$ C. to about $0°$ C. by treating II with a strong base such as lithium diisopropylamide, lithium hexamethyldisilazide, sodium amide, or the like. When $R_3$ is $C_1-C_3$ alkyl, one molar equivalent of base is required; when $R_3$ is hydrogen, two molar equivalents are employed. The anion of II is then treated with $R_1X$ in the usual manner to prepare the alkylated intermediate III.

Intermediate III may be transformed to intermediate IV using the same general alkylation procedure described above. When m is 0, the alkylating agent is benzyl- or 4-methoxybenzyl-disulfide. When m is 1, the alkylating agent is a benzyl or 4-methoxybenzyl halomethyl sulfide $R_4SCH_2X$. When m is 0, the order of the two alkylation steps described above may be reversed although the sequence as described in Scheme I is preferred. When m is 1, the alkylation steps can not be reversed since attempts to form the anion of a mercapto intermediate related to formula IV (m=1, $R_1$=hydrogen), result in elimination of the $R_4$—S-functionality.

The deblocking of the thiol functionality in IV may be accomplished in two ways. When $R_4$ is benzyl, the deblocking is usually done by dissolving IV in a nonreactive low melting solvent such as tetrahydrofuran, adding liquid ammonia, and dissolving elemental sodium. Sodium in refluxing t-butanol or ethanol or hydrogen fluoride in anisole may also be employed. Alternatively, when $R_4$ is 4-methoxybenzyl, especially when m=0, the protecting group may be removed by treating with trifluoromethylsulfonic acid in a solvent such as anisole and/or methylene chloride.

Although the above scheme is preferably carried out on the corresponding acid derivatives ($R_3$ is hydrogen), the sequence may also be performed on the corresponding ester derivatives ($R_3$ is $C_1-C_3$ alkyl). The intraconversions of the acid and ester forms of I may be performed by the usual methods known in the art.

An additional method of preparing the compounds of formula I is described in Scheme II:

or ethyl, and $R_3'$ is $C_1-C_3$ alkyl. The acetal-ester V is subjected to the alkylation procedures previously described for Scheme I. Thus, V may be alkylated alpha to the ester functionality to provide a compound of formula VI. Intermediate VI may then be alkylated with the appropriate $R_4$-disulfide as previously described to provide the corresponding dialkylated intermediate VIIIb. In a similar way, VI may be alkylated with a dihalomethane to provide the halomethyl intermediate VII which on treatment with a $R_4$-sulfide in the presence of an acid scavenger, such as potassium carbonate, in a nonreactive solvent, such as dimethylformamide, provides intermediate VIIIa. Alternatively, VIIIa may be prepared directly from VI by alkylating with $R_4SCH_2X$ in the usual way. Intermediates VIIIa and VIIIb are then transformed to the aldehyde-ester IX by acidic hydrolysis. The reaction of the aldehyde-ester IX with the amino acid ester XI in a nonreactive solvent such as methanol provides an intermediate Schiff base derivative which, upon treatment with a mild reducing agent such as sodium borohydride in methanol, provides the corresponding uncyclized amine-ester which on heating in a nonreactive high boiling solvent such as toluene provides the desired lactam IV where $R_3$ is $C_1-C_3$ alkyl. This lactam intermediate may then be transformed into compounds of formula I by methods as previously described.

The acid derivatives ($R_3$ is hydrogen) may be transformed into pharmaceutically acceptable salts by treatment with the appropriate base in any of a number of ways known in the art. Basic agents suitably employed in salt formation belong to both the organic and inorganic types and include ammonia, organic amines, alkali and alkaline earth metal hydroxides, hydrides, and alkoxides, alkali metal bicarbonates, and alkaline earth metal carbonates. The preferred salts include ammonium, sodium, and potassium.

The intermediates and reagents used in the above reactions are known in the art or can be prepared by Scheme II

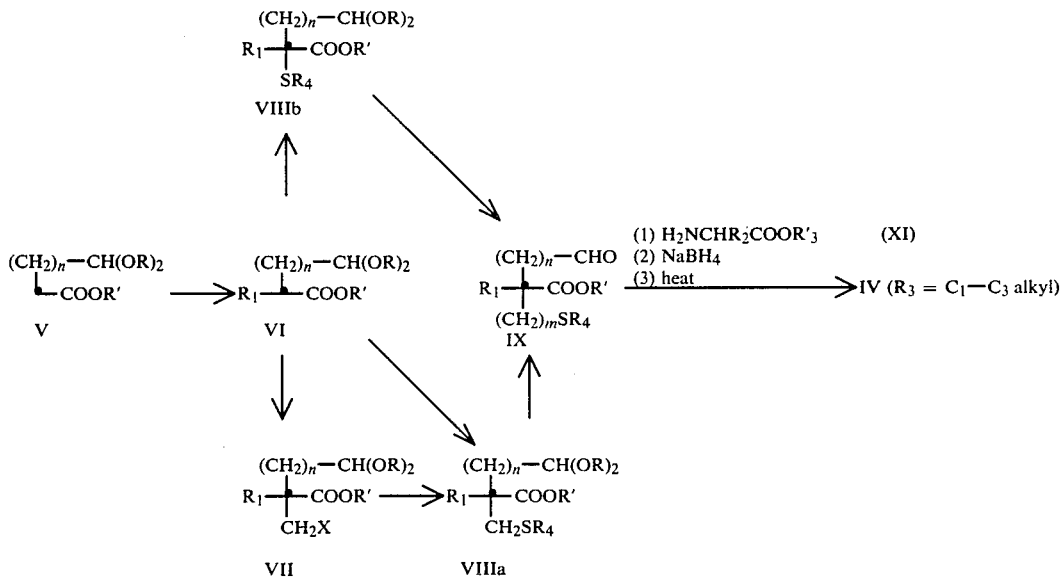

wherein
$R_1$, $R_2$, $R_4$, m, n, and X are the same as described hereinabove, each of R and R' is independently methyl methods known in the art. Thus, intermediate lactam derivatives II can be prepared by alkylating an unsubstituted lactam with an α-halo amino acid derivative. Alternatively, the compounds of formula II may be prepared by the reaction of the appropriate amino acid with an omega-halo acid derivative. The acetal-ester derivatives of formula V are prepared from the corresponding aldehyde-esters which are in turn prepared from the corresponding omega-hydroxy esters. Alternatively, compounds V may be prepared by reacting the acetal derivative of an omega-haloalkylaldehyde with a malonic ester in the presence of a base followed by decarboxylation in the usual way.

The compounds may be administered by various routes including the oral, rectal, transdermal, subcutaneous, intravenous, intramuscular, or intranasal routes, being usually employed in the form of a pharmaceutical composition. Such compositions are prepared in a manner well known in the pharmaceutical art and comprise at least one active compound. Accordingly, the invention includes a pharmaceutical composition comprising as active ingredient a compound of formula I associated with a pharmaceutically acceptable carrier.

In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the composition can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers are lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propyl-hydroxybenzoates, talc, magnesium stearate or mineral oil. The formulations can additionally include lubricating agents, wetting agents, emulsifying and suspending agents, preserving agents, sweetening agents or flavoring agents. The compositions of the invention may, as is well known in the art, be formulated so as to provide quick, sustained or delayed release of the active ingredient after administration to the patient.

Preferably the compositions are formulated in a unit dosage form, each dosage containing from about 5 to 500 mg., more usually about 25 to 300 mg., of the active ingredient. The term "unit dosage form" refers to physically discrete units suitable as unitary dosages for human subjects and animals, each unit containing a predetermined quantity of active material calculated to produce the desired therapeutic effect, in association with the required pharmaceutical carrier.

The active compounds are effective over a wide dosage range. For example, dosages per day will normally fall within the range of about 0.5 to 300 mg./kg. In the treatment of adult humans, the range of about 1 to 50 mg./kg., in single or divided doses, is preferred. However, it will be understood that the amount of the compound actually administered will be determined by a physician, in the light of the relevant circumstances including the condition to be treated, the choice of compound to be administered, the chosen route of administration, the age, weight, and response of the individual patient, and the severity of the patient's symptoms, and therefore the above dosage ranges are not intended to limit the scope of the invention in any way.

In an effort to more fully illustrate this invention, the following detailed examples are provided. The examples are illustrative only and are not intended to limit the scope of the invention in any way.

EXAMPLE 1

(αS)-3-(mercaptomethyl)-α,3-dimethyl-2-oxo-1-pyrrolidineacetic acid

A. Preparation of N-(4-chlorobutanoyl)-1-alanine.

A solution of 17.8 g. of 1-alanine hydrochloride in 200 ml. of water and 200 ml. of tetrahydrofuran was cooled in an ice bath and brought to pH 9 with 2N sodium hydroxide. The solution was then treated with the alternate addition of approximate 1.5 ml. portions of 4-chlorobutyryl chloride and sufficient 2N sodium hydroxide to maintain the pH at 9. A total of 22.4 ml. of the acid chloride and approximately 200 ml. of 2N sodium hydroxide were added. When the addition was complete, the mixture was stirred at room temperature for ten minutes and then poured into a separatory funnel. The pH was adjusted to 1.0–1.5 by the addition of 28 ml. of hydrochloric acid. The mixture was extracted three times each with 200 ml. of chloroform. The organic extracts were combined and washed with 50 ml. of 1N hydrochloric acid followed by washing with 50 ml. of a saturated sodium chloride solution. The organic layer was dried over sodium sulfate and the solvent was removed by evaporation in vacuo to yield 28.4 g. of the desired chloroamide as an oil.

B. Preparation of α(S)-methyl-2-oxo-1-pyrrolidineacetic acid

A solution of lithium diisopropylamide was prepared in the usual manner from 15.4 ml. of diisopropylamine, 65.6 ml. of 1.6M n-butyllithium in hexane, and 100 ml. of dry tetrahydrofuran at −20° C. The solution was cooled to −65° C. and a solution of 9.7 g. of N-(4-chlorobutanoyl)-1-alanine and 8.65 ml. of hexamethylphosphoramide in 20 ml. of tetrahydrofuran was added over a ten minute period. When the addition was complete, the reaction was allowed to warm to room temperature and was stirred for four hours. The reaction mixture was poured into 100 ml. of a saturated sodium chloride solution and extracted with three 100 ml. portions of chloroform. The aqueous layer was then acidified with 35 ml. of 2N hydrochloric acid and extracted with three 150 ml. portions of chloroform. The combined chloroform acid extracts were dried over sodium sulfate and the solvent was removed in vacuo. The residue was triturated with diethyl ether to provide 3.1 g. of the desired lactam, m.p. about 141.5°–146.5° C.

C. Preparation of (αS)-α,3-dimethyl-2-oxo-1-pyrrolidineacetic acid.

Following the general procedure of Example 1B, 80 mmoles (12.6 g.) of α(S)-methyl-2-oxo-1-pyrrolidineacetic acid were treated with 160 mmoles of lithium diisopropylamide in tetrahydrofuran. The resulting dianion was then treated with 11.38 g. of methyl iodide and 14 ml. of hexamethylphosphoramide in tetrahydrofuran. The reaction was then worked up in the usual manner. The material was purified by two crystallizations from ethyl acetate affording 5.5 g. of the desired intermediate, m.p. about 149°–150° C.

D. Preparation of (αS)-3-(benzylmercaptomethyl)-α,3-dimethyl-2-oxo-1-pyrrolidineacetic acid.

Following the general procedure of Example 1C, 6.84 g. (40 mmoles) of (αS)-α,3-dimethyl-2-oxo-1-pyrrolidineacetic acid were treated first with 80 mmoles of lithium diisopropylamide in tetrahydrofuran which was then followed with the addition of 9.55 g. of benzylmercaptomethyl bromide and 13.9 ml. of hexamethylphosphoramide in tetrahydrofuran. Purification by high pressure liquid chromatography gave 2 g. of the desired title intermediate.

E. Preparation of (αS)-3-(mercaptomethyl)-α,3-dimethyl-2-oxo-1-pyrrolidineacetic acid.

Two grams of (αS)-3-(benzylmercaptomethyl)α,3-dimethyl-2-oxo-1-pyrrolidineacetic acid were dissolved in about 15 ml. of tetrahydrofuran. This solution was then added to liquid ammonia. Small pieces of sodium metal were added until a blue color persisted. The reaction was then quenched by the addition of about two grams of ammonium chloride. The ammonia was evaporated and water was added to the residue. The slurry was made acidic with hydrochloric acid, saturated with sodium chloride and the acidic solution was extracted with chloroform. The chloroform extract was washed with a saturated sodium chloride solution, dried over magnesium sulfate and evaporated to dryness. Two crystallizations of the resulting solid from diethylether/Skelly B gave 0.5 g. of the desired title product, m.p. about 132°–133° C. $[\alpha]_D^{25} = -23.78°$ (c=1, methanol).

Analysis: $C_9H_{15}NO_3S$; Calc.: C, 49.75; H, 6.96; N, 6.45; S, 14.76; Found: C, 49.67; H, 7.29; N, 6.31; S, 14.55.

EXAMPLE 2

(αS)-3-ethyl-3-(mercaptomethyl)-α-methyl-2-oxo-1-pyrrolidineacetic acid

Following the procedures of Examples 1C–1E, α(S)-methyl-2-oxo-1-pyrrolidineacetic acid was first alkylated with ethyl iodide and then with benzylmercaptomethyl bromide. Removal of the benzyl group in the usual way and purification by chromatography provided the title compound as a mixture of diastereomers. $[\alpha]_D^{25} = -4.04°$ (c=1, methanol).

Analysis: $C_{10}H_{17}NO_3S$; Calc.: C, 51.93; H, 7.41; N, 6.06; Found: C, 51.78; H, 7.12; N, 5.78.

EXAMPLES 3 AND 4

(αS,3R)-3-(mercaptomethyl)-α-methyl-2-oxo-3-benzyl-1-pyrrolidineacetic acid and
(S,S)-3-(mercaptomethyl)-α-methyl-2-oxo-3-benzyl-1-pyrrolidine-acetic acid A. Preparation of ethyl 2-benzyl-4,4-diethoxybutyrate.

A solution of 27.7 g. of ethyl 4,4-diethoxybutyrate in 20 ml. of tetrahydrofuran was added to 142 mmoles of lithium diisopropylamide prepared in the usual manner from diisopropylamine and n-butyllithium in tetrahydrofuran at −60° C. After stirring the reaction for 2.5 hours at about −70° C., 25.3 g. of benzyl bromide in 25.8 ml. of hexamethylphosphoramide were added over a ten minute period. The reaction was stirred an additional hour at −75° C. The reaction mixture was poured into one liter of hexane and was washed successively with 100 ml. of 2N hydrochloric acid, 50 ml. of 2N hydrochloric acid, 50 ml. of 10% aqueous sodium bicarbonate, and 100 ml. of a saturated sodium chloride solution. The organic layer was dried over sodium sulfate and evaporated in vacuo. The residue was distilled at 0.05 torr until the temperature of the distillate reached 85° C. Signs of decomposition were evident and distillation was discontinued. The pot residue contained 25.5 g. of the desired intermediate which was used without further purification.

B. Preparation of ethyl 2-benzyl-2-chloromethyl-4,4-diethoxybutyrate.

A solution of 25.5 g. of ethyl 2-benzyl-4,4-diethoxybutyrate in 15.6 g. of hexamethylphosphoramide was added to 96 mmoles of lithium diisopropylamide in tetrahydrofuran. The resulting anion was treated with 13.0 g. of bromochloromethane at −70° C. After stirring the reaction for one hour at −70° C., the reaction was allowed to warm to room temperature. The reaction was worked up in the usual way to afford 26.7 of the chloromethylated intermediate which was used without further purification.

C. Preparation of ethyl 2-benzyl-2-[(4-methoxybenzyl)mercaptomethyl]-4,4-diethoxybutyrate.

A solution of 26.7 g. of ethyl 2-benzyl-2-chloromethyl-4,4-diethoxybutyrate, 24 g. of 4-methoxybenzylmercaptan, and 21.5 g. of potassium carbonate in 250 ml. of dimethylformamide was heated to reflux for six hours. The cooled mixture was poured into a mixture of about 90 ml. of hexane and 15 ml. of a saturated sodium chloride solution. The layers were separated. The hexane layer was washed first with 1N sodium hydroxide and then with a saturated sodium chloride solution. After drying over sodium sulfate, the solvent was removed in vacuo. The crude product was chromatographed over silica gel affording 9.0 g. of the desired intermediate as a light orange oil.

D. Preparation of ethyl 2-benzyl-2-[(4-methoxybenzyl)mercaptomethyl]-4-oxo-butyrate.

A solution of 4.6 g. of ethyl 2-benzyl-2-[(4-methoxybenzyl)mercaptomethyl]-4,4-diethoxybutyrate in 75 ml. of acetone and 30 ml. of 3N hydrochloric acid was stirred at room temperature for about 30 minutes. Most of the acetone was then removed by evaporation under reduced pressure and the remaining aqueous solution was extracted twice each with a mixture of 60 ml. of diethyl ether and 20 ml. of toluene. The organic extracts were combined and washed successively with 25 ml. of 10% sodium bicarbonate and 25 ml. of a saturated sodium chloride solution. The organic layer was dried over sodium sulfate and removed in vacuo to afford 3.8 g. of the desired aldehyde which was used directly in the next step.

E. Preparation of N-(3-ethoxycarbonyl-3-[(4-methoxybenzyl)mercaptomethyl]-4-phenylbutyl)-1-alanine ethyl ester.

A solution of 1.53 g. of 1-alanine ethyl ester hydrochloride in 15 ml. of methanol was cooled in an ice bath. A solution of 1.83 g. of dicyclohexylamine in 5 ml. of methanol was added followed by the addition of 3.8 g. of the aldehyde intermediate isolated in Example 3/4D above. The reaction was stirred at room temperature for two hours. The methanol was then removed by evaporation under reduced pressure. The residue was taken up in ether and filtered. The solvent was removed from the filtrate to afford 4.79 g. of the Schiff base adduct which was then dissolved in 30 ml. of methanol. The solution was cooled by means of an external ice bath, and 0.74 g. of sodium borohydride was added. The reaction was stirred at room temperature for about 17 hours at which time the methanol was removed by evaporation in vacuo. The residue was taken up in methylene chloride, washed several times with water, dried over sodium sulfate, and the solvent was removed under reduced pressure to afford 4.07 g. of the desired N-substituted alanine ester which was used without further purification.

F. Preparation of ethyl(αS)-3-[(4-methoxybenzyl)-mercaptomethyl]-α-methyl-2-oxo-3-benzyl-1-pyrrolidineacetate.

The 4.07 g. of the N-substituted alanine ester from the preceding procedure were dissolved in 50 ml. of toluene and allowed to reflux under a nitrogen atmosphere for 24 hours. The toluene was removed by evaporation under reduced pressure and the residue was purified by chromatography over silica gel eluting with 20% ethyl acetate in toluene providing 2.17 g. of the desired pyrrolidine intermediate.

G. Preparation of (αS,3R)-3-(mercaptomethyl)-α-methyl-2-oxo-3-benzyl-1-pyrrolidineacetic acid and (S,S)-3-mercaptomethyl)-α-methyl-2-oxo-3-benzyl-1-pyrrolidineacetic acid.

The 2.17 g. of the pyrrolidine intermediate from the preceding procedure were dissolved in 50 ml. of tetrahydrofuran and cooled with an external ice bath. The solution was treated with 12.5 ml. of 1N sodium hydroxide. The ice bath was removed and stirring was continued for 18 hours at room temperature. The mixture was poured into 50 ml. of a saturated sodium chloride solution to which 12 ml. of 2N hydrochloric acid had been added. The aqueous solution was extracted twice with 100 ml. portions of methylene chloride. The combined organic extracts were washed with 50 ml. of a saturated sodium chloride solution, dried over sodium sulfate, and the solvent was removed in vacuo. The residue was dissolved in 50 ml. of methylene chloride and cooled by means of an external ice bath. To the solution were added 2.67 g. of anisole followed by the addition of 3.3 ml. of trifluoromethylsulfonic acid. After stirring under a nitrogen atmosphere for five minutes, the ice bath was removed and stirring was continued at room temperature for an additional 45 minutes. The solution was poured into 100 ml. of chloroform to which 50 ml. of a saturated sodium chloride solution had been added. The layers were separated and the aqueous layer was further extracted with two 100 ml. portions of chloroform. The combined organic extracts were washed with 50 ml. of a sodium chloride solution, dried over sodium sulfate, and the solvent was removed in vacuo. The resulting oil was chromatographed over silica gel eluting with 5% acetic acid in chloroform. Certain of the earlier fractions were combined and evaporated to provide 0.3 g. of (αS,3R)-3-(mercaptomethyl)-α-methyl-2-oxo-3-benzyl-1-pyrrolidineacetic acid as a white solid, m.p. about 131°–135.5° C. Certain of the later eluting fractions were combined and evaporated to provide 0.3 g. of the corresponding (S,S)diastereomer as a white solid, m.p. about 139.5°–145.5° C. The NMR spectra were consistent with the structures of the respective compounds.

The following formulation examples may employ as active compounds any of the pharmaceutical compounds of the invention.

EXAMPLE 5

Hard gelatin capsules are prepared using the following ingredients:

|  | Quantity (mg./capsule) |
|---|---|
| Active compound | 250 |
| Starch dried | 200 |
| Magnesium stearate | 10 |

The above ingredients are mixed and filled into hard gelatin capsules in 460 mg. quantities.

EXAMPLE 6

A tablet formula is prepared using the ingredients below:

|  | Quantity (mg./tablet) |
|---|---|
| Active compound | 250 |
| Microcrystalline cellulose | 400 |
| Silicon dioxide, fumed | 10 |
| Stearic acid | 5 |

The components are blended and compressed to form tablets each weighing 665 mg.

EXAMPLE 7

An aerosol solution is prepared containing the following components:

|  | Weight % |
|---|---|
| Active ingredient | 0.25 |
| Ethanol | 29.75 |
| Propellant 22 (Chlorodifluoromethane) | 70 |

The active compound is mixed with ethanol and the mixture added to a portion of the propellant 22, cooled to −30° C. and transferred to a filling device. The required amount is then fed to a stainless steel container and diluted further with the remainder of the propellant. The valve units are then fitted to the container.

EXAMPLE 8

Tablets each containing 60 mg. of active ingredient are made up as follows:

| Active ingredient | 60 mg. |
|---|---|
| Starch | 45 mg. |
| Microcrystalline cellulose | 35 mg. |
| Polyvinylpyrrolidone (as 10% solution in water) | 4 mg. |
| Sodium carboxymethyl starch | 4.5 mg. |
| Magnesium stearate | 0.5 mg. |
| Talc | 1 mg. |
| Total | 150 mg. |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

EXAMPLE 9

Capsules each containing 80 mg. of medicament are made as follows:

| | |
|---|---|
| Active ingredient | 80 mg. |
| Starch | 59 mg. |
| Microcrystalline cellulose | 59 mg. |
| Magnesium stearate | 2 mg. |
| Total | 200 mg. |

The active ingredient, cellulose, starch and magnesium stearate are blended, passed through a No. 45 mesh U.S. sieve, and filled into hard gelatin capsules in 200 mg. quantities.

EXAMPLE 10

Suppositories each containing 225 mg. of active ingredient are made as follows:

| | |
|---|---|
| Active ingredient | 225 mg. |
| Saturated fatty acid glycerides to | 2,000 mg. |

The active ingredient is passed through a No. 60 mesh U.S. sieve and suspended in the saturated fatty acid glycerides previously melted using the minimum heat necessary. The mixture is then poured into a suppository mold of nominal 2 g. capacity and allowed to cool.

EXAMPLE 11

Suspension each containing 50 mg. of medicament per 5 ml. dose are made as follows:

| | |
|---|---|
| Active ingredient | 50 mg. |
| Sodium carboxymethyl cellulose | 50 mg. |
| Syrup | 1.25 ml. |
| Benzoic acid solution | 0.10 ml. |
| Flavor | q.v. |
| Color | q.v. |
| Purified water to | 5 ml. |

The medicament is passed through a No. 45 mesh U.S. sieve and mixed with the sodium carboxymethylcellulose and syrup to form a smooth paste. The benzoic acid solution, flavor and color are diluted with some of the water and added, with stirring. Sufficient water is then added to produce the required volume.

The compounds of this invention and their pharmaceutically acceptable salts have been found to possess useful pharmaceutical properties. The compounds are useful in the treatment of hypertension and congestive heart failure by virtue of their ability to inhibit angiotensin converting enzyme. In addition to inhibiting the conversion of angiotensin I to angiotensin II, the compounds inhibit the degradation of bradykinin and enkephalins and are therefore useful in the treatment of disorders associated with an imbalance in levels of these agents as well. Certain compounds of the present invention were examined as to their ability to inhibit angiotensin converting enzyme in the following test system.

ASSAY OF INHIBITORS OF ANGIOTENSIN CONVERTING ENZYME

The procedure for the assay of angiotensin I converting enzyme activity was essentially that described by Cheung and Cushman, Biochemica et Biophysica Acta, 293, 451–463 (1973). The enzyme was isolated from rabbit lung and purified via calcium phosphate gel, and DEAE-cellulose column chromatography. Human angiotensin I was employed as the substrate. The assay is dependent on the fluorometric measurement of the rate of release of the dipeptide histidylleucine from the substrate by the enzyme when the released dipeptide is reacted with o-phthalicdicarboxaldehyde. A standard curve is prepared with known quantities of histidylleucine.

Incubations were conducted at 37° C. in $13 \times 100$ mm. test tubes containing a final volume of 250 $\mu$l. The conditions of the assay employed were as follows: 100 $\mu$l. of 0.3 mM angiotensin I dissolved in saline-phosphate buffer (30 mM NaCl, 100 mM potassium phosphate, pH 7.5) and 50 $\mu$l. of saline-phosphate buffer (or test compound dissolved in the buffer) were allowed to stand at least three minutes at ambient temperature. The enzymic reaction was initiated by adding 100 $\mu$l. of enzyme solution containing 25 to 50 $\mu$g. protein/ml., determined by the Lowry method. The tubes were incubated for 30 minutes at 37° C. The reaction was terminated by adding 1.45 ml. of 300 mM NaOH followed with 100 $\mu$l. of 0.2 percent o-phthalicdicarboxaldehyde in methanol. After ten minutes, 200 $\mu$l. of 3M HCl were added. The final volume in the tubes was 2 ml. Fluorometric determinations (365 nm excitation and 500 nm emission) were made after 30 minutes but within 90 minutes after termination of the reaction.

The concentration of the inhibitors were adjusted so that a range of concentrations of $10^{-4}$ to $10^{-9}$M was obtained in the reaction tubes. Inhibition was measured by the decrease in activity from that of control tubes without inhibitor. Activity was recorded as the molar concentration of inhibitor producing a 50 percent decrease in converting enzyme activity relative to the controls and is summarized in Table I.

TABLE I

| Inhibition of Angiotensin Converting Enzyme | |
|---|---|
| Compound of Example No. | Concentration giving 50% Inhibition of Conversion of Angiotensin I to Angiotensin II |
| 1 | $1.0 \times 10^{-6}$ M |
| 2 | $2.0 \times 10^{-6}$ M |
| 3 | $5.0 \times 10^{-6}$ M |
| 4 | $>1.0 \times 10^{-4}$ M |

I claim:

1. A compound of the formula I

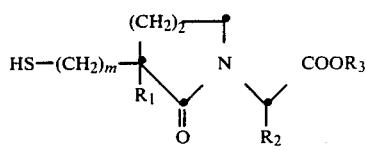

and pharmaceutically acceptable salts thereof wherein
    m is 0 or 1;
    n is 1;
    $R_1$ is $C_1$–$C_3$ alkyl or benzyl;
    $R_2$ is hydrogen or $C_1$–$C_3$ alkyl; and
    $R_3$ is hydrogen or $C_1$–$C_3$ alkyl.
2. A compound of claim 1 wherein m is 1.
3. A compound of claim 2 wherein $R_3$ is hydrogen.
4. A compound of claim 3 wherein $R_2$ is methyl.
5. A compound of claim 4 wherein $R_1$ is $C_1$–$C_3$ alkyl.

6. A compound of claim 5 wherein $R_1$ is methyl.

7. The compound of claim 6 which is ($\alpha$S)-3-(mercaptomethyl)-$\alpha$,3-dimethyl-2-oxo-1-pyrrolidineacetic acid or a pharmaceutically acceptable salt thereof.

8. The compound of claim 5 which is ($\alpha$S)-3-ethyl-3-(mercaptomethyl)-$\alpha$-methyl-2-oxo-1pyrrolidine-acetic acid or a pharmaceutically acceptable salt thereof.

9. The compound of claim 4 which is ($\alpha$S,3R)-3-(mercaptomethyl)-$\alpha$-methyl-2-oxo-3-benzyl-1-pyrrolidineacetic acid or a pharmaceutically acceptable salt thereof.

10. A method of treating hypertension comprising administering to a mammal suffering from hypertension and in need of treatment an effective amount of a compound according to claim 1.

11. A formulation which comprises a compound of claim 1 in combination with a suitable pharmaceutical carrier, diluent, or excipient.

12. A formulation according to claim 11 wherein m is 1.

13. A formulation according to claim 12 wherein $R_3$ is hydrogen.

14. A formulation according to claim 13 wherein $R_2$ is methyl.

15. A formulation according to claim 14 wherein $R_1$ is $C_1$-$C_3$ alkyl.

16. A formulation according to claim 15 wherein the compound is ($\alpha$S)-3-(mercaptomethyl)-$\alpha$,3-dimethyl-2-oxo-1-pyrrolidineacetic acid or a pharmaceutically acceptable salt thereof.

17. A formulation according to claim 15 wherein the compound is ($\alpha$S)-3-ethyl-3-(mercaptomethyl)-$\alpha$-methyl-2-oxo-1-pyrrolidineacetic acid or a pharmaceutically acceptable salt thereof.

18. A formulation according to claim 14 wherein the compound is ($\alpha$S,3R)-3-(mercaptomethyl)-$\alpha$-methyl-2-oxo-3-benzyl-1-pyrrolidineacetic acid or a pharmaceutically acceptable salt thereof.

* * * * *